(12) United States Patent
Sharp et al.

(10) Patent No.: US 10,893,901 B2
(45) Date of Patent: *Jan. 19, 2021

(54) SURGICAL INSTRUMENT WITH DISPENSABLE COMPONENTS

(71) Applicant: COVIDIEN LP, Mansfield, MA (US)

(72) Inventors: Robert M. Sharp, Boulder, CO (US); William H. Nau, Jr., Longmont, CO (US); Glenn A. Horner, Boulder, CO (US); Duane E. Kerr, Loveland, CO (US); Kristel L. Ambrosius, Cary, NC (US)

(73) Assignee: Covidien LP, Mansfield, MA (US)

( * ) Notice: Subject to any disclaimer, the term of this patent is extended or adjusted under 35 U.S.C. 154(b) by 243 days.

This patent is subject to a terminal disclaimer.

(21) Appl. No.: 16/102,668

(22) Filed: Aug. 13, 2018

(65) Prior Publication Data

US 2018/0344388 A1    Dec. 6, 2018

Related U.S. Application Data

(63) Continuation of application No. 13/028,810, filed on Feb. 16, 2011, now Pat. No. 10,045,811.

(51) Int. Cl.
*A61B 18/14* (2006.01)
*A61B 17/00* (2006.01)
*A61B 18/00* (2006.01)

(52) U.S. Cl.
CPC .. *A61B 18/1445* (2013.01); *A61B 2017/0023* (2013.01); *A61B 2018/0063* (2013.01);
(Continued)

(58) Field of Classification Search
CPC ...... A61B 18/1445; A61B 2018/00601; A61B 2018/0063; A61B 2018/1455; A61B 2018/1495; A61B 2017/0023
(Continued)

(56) References Cited

U.S. PATENT DOCUMENTS 4,120,302 A   10/1978 Ziegler
4,509,518 A   4/1985 McGarry et al.
(Continued)

FOREIGN PATENT DOCUMENTS

CN   2548592 Y   5/2003
CN   1525839 A   9/2004
(Continued)

OTHER PUBLICATIONS

Chinese Office Action for application No. 20171071 2357.6 dated May 6, 2020 with English translation.
(Continued)

*Primary Examiner* — Michael F Peffley
*Assistant Examiner* — Khadijeh A Vahdat
(74) *Attorney, Agent, or Firm* — Carter, DeLuca & Farrell LLP

(57) ABSTRACT

A surgical instrument includes an active electrode coupled to a source of electrosurgical energy. The active electrode includes a tissue-contacting surface on an exterior surface of the instrument such that the tissue-contacting surface of the active electrode may intimately engage tissue. A replacement electrode includes a tissue-contacting surface, and is located in an interior cavity of the instrument. A seal is formed between the active electrode and the interior cavity of the instrument such that the tissue-contacting-surface of the replacement electrode is isolated from contamination exposed to the exterior of the instrument. The active electrode is removable from the instrument to expose the tissue-contacting surface of the replacement electrode, and the replacement electrode is connectable to the source of electrosurgical energy when the active electrode is removed.

5 Claims, 7 Drawing Sheets

(52) U.S. Cl.
CPC ............... *A61B 2018/00601* (2013.01); *A61B 2018/1455* (2013.01); *A61B 2018/1495* (2013.01)

(58) Field of Classification Search
USPC ..................................................... 606/41–52
See application file for complete search history.

(56) References Cited

U.S. PATENT DOCUMENTS

| | | | |
|---|---|---|---|
| 5,125,927 A * | 6/1992 | Belanger ............ | A61B 18/1402 606/45 |
| 5,201,900 A | 4/1993 | Nardella | |
| 5,250,072 A | 10/1993 | Jain | |
| 5,330,495 A | 7/1994 | Dettwiler et al. | |
| 5,509,920 A | 4/1996 | Phillips et al. | |
| 5,876,401 A | 3/1999 | Schulze et al. | |
| 6,050,996 A | 4/2000 | Schmaltz et al. | |
| 6,530,942 B2 | 3/2003 | Fogarty et al. | |
| 7,306,599 B2 | 12/2007 | Karasawa et al. | |
| 7,347,858 B2 | 3/2008 | Francischelli et al. | |
| 7,442,193 B2 | 10/2008 | Shields et al. | |
| 7,481,810 B2 | 1/2009 | Dumbauld et al. | |
| 7,727,231 B2 | 6/2010 | Swanson | |
| 7,862,561 B2 | 1/2011 | Swanson et al. | |
| 7,877,853 B2 | 2/2011 | Unger et al. | |
| 10,045,811 B2 | 8/2018 | Sharp et al. | |
| 2002/0120267 A1 | 8/2002 | Phan | |
| 2002/0165549 A1 | 11/2002 | Owusu-Akyaw et al. | |
| 2003/0109875 A1 | 6/2003 | Tetzlaff et al. | |
| 2003/0231990 A1 | 12/2003 | Faries | |
| 2005/0004570 A1 | 1/2005 | Chapman et al. | |
| 2005/0240178 A1 | 10/2005 | Morley et al. | |
| 2006/0195081 A1 | 8/2006 | Landis et al. | |
| 2006/0271102 A1 | 11/2006 | Bosshard et al. | |
| 2007/0261174 A1 | 11/2007 | Barker | |
| 2008/0071269 A1 | 3/2008 | Hilario et al. | |
| 2009/0088744 A1 | 4/2009 | Townsend | |
| 2009/0125012 A1 | 5/2009 | Rioux et al. | |
| 2009/0182331 A1 | 7/2009 | D'Amelio et al. | |
| 2010/0198248 A1 | 8/2010 | Vakharia | |
| 2010/0217260 A1 | 8/2010 | Aramayo | |
| 2010/0292691 A1 | 11/2010 | Brogna | |
| 2011/0098689 A1 | 4/2011 | Nau, Jr. et al. | |
| 2011/0276049 A1 | 11/2011 | Gerhardt | |
| 2012/0017923 A1 * | 1/2012 | Sobe ....................... | A61B 34/20 128/899 |
| 2013/0046295 A1 | 2/2013 | Kerr et al. | |
| 2013/0072919 A1 | 3/2013 | Allen, IV et al. | |

FOREIGN PATENT DOCUMENTS

| | | |
|---|---|---|
| CN | 1681447 A | 10/2005 |
| CN | 101098662 A | 1/2008 |
| CN | 201088624 Y | 7/2008 |

OTHER PUBLICATIONS

European Search Report EP12155756 dated Jun. 25, 2012.
Chinese Office Action dated Mar. 30, 2015, 9 pages.
European Office Action for EP 12 155 756.5 dated Sep. 18, 2015.
Chinese Office Action for application No. 201510028228.6 dated May 31, 2016.
Chinese Office Action for application No. 201710712357.6 dated Aug. 22, 2019 with English translation.

* cited by examiner

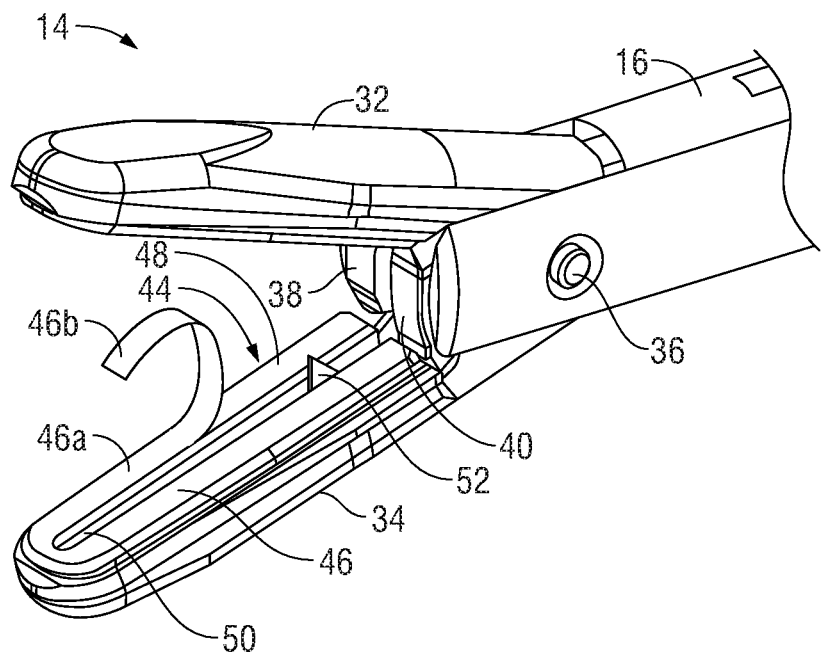
FIG. 2
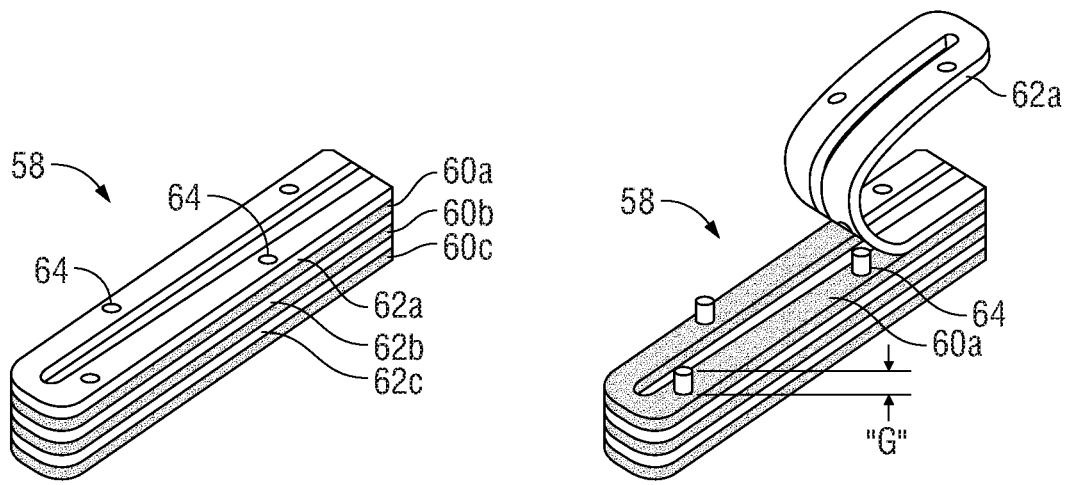
FIG. 3A
FIG. 3B

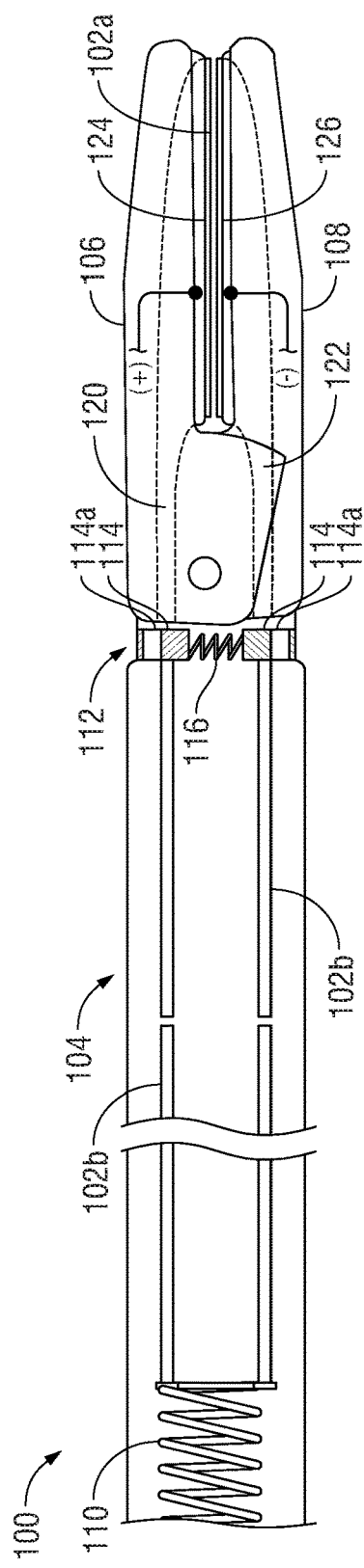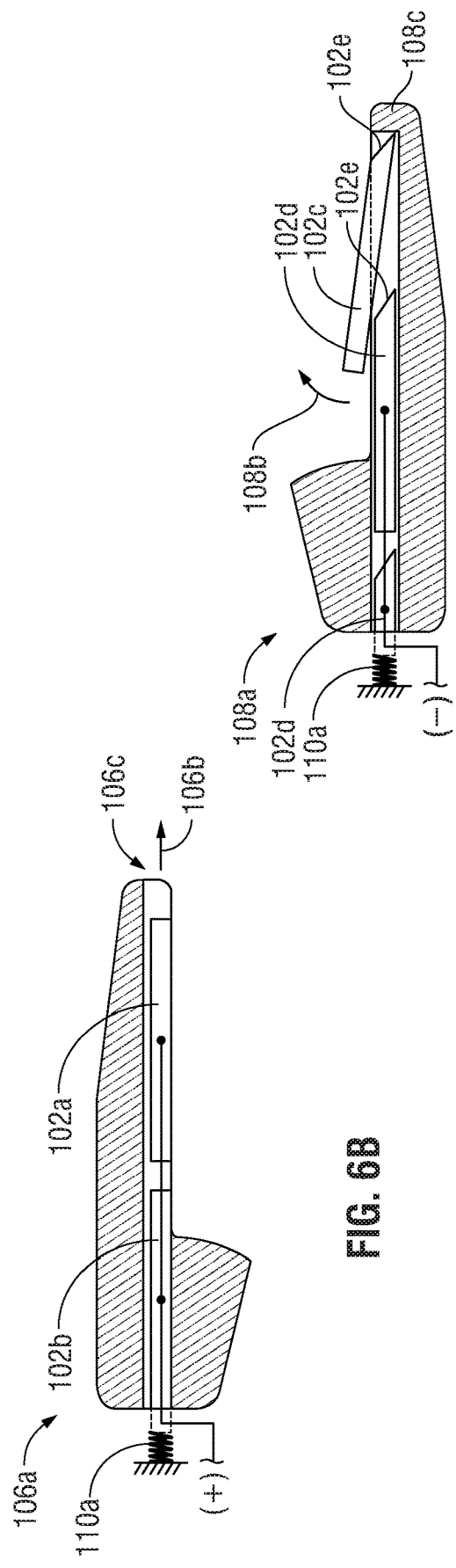

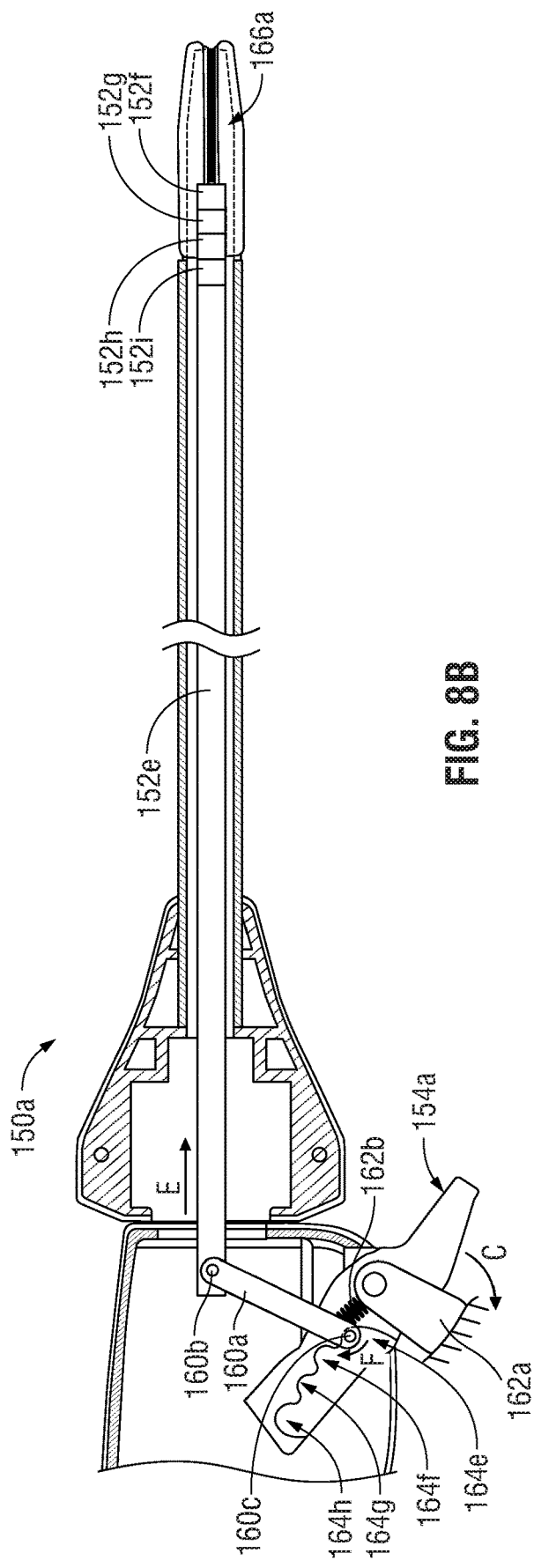
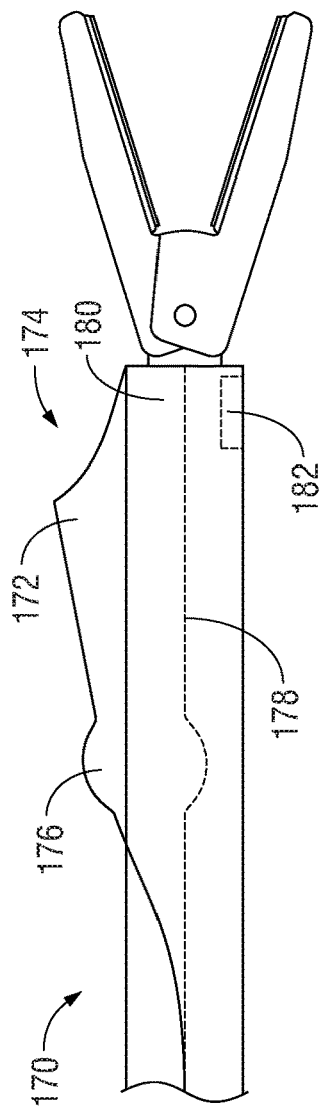
FIG. 8B
FIG. 9

(19) United States
US 10,893,901 B2

SURGICAL INSTRUMENT WITH DISPENSABLE COMPONENTS

CROSS-REFERENCE TO RELATED APPLICATION

The present application is a Continuation Application which claims the benefit of and priority to U.S. patent application Ser. No. 13/028,810, filed on Feb. 16, 2011, the entire content of which is incorporated herein by reference.

BACKGROUND

1. Technical Field

The present disclosure relates generally the field of reusable surgical instruments. In particular, the disclosure relates to instruments with dispensable components to provide clean, sterile or refurbished surfaces in each instance of use.

2. Background of Related Art

Instruments such as electrosurgical forceps are commonly used in open and endoscopic surgical procedures to coagulate, cauterize and seal tissue. Such forceps typically include a pair of jaws that can be controlled by a surgeon to grasp targeted tissue, such as, e.g., a blood vessel. The jaws may be approximated to apply a mechanical clamping force to the tissue, and are associated with at least one electrode surface to permit the delivery of electrosurgical energy to the tissue. The combination of the mechanical clamping force and the electrosurgical energy has been demonstrated to join adjacent layers of tissue captured between the jaws. When the adjacent layers of tissue include the walls of a blood vessel, sealing the tissue may result in hemostasis. Thereafter, the sealed tissue may be transected by advancing a knife through the jaws. A detailed discussion of the use of an electrosurgical forceps may be found in U.S. Pat. No. 7,255,697 to Dycus et al.

In use, various tissue-contacting components of an electrosurgical forceps tend to become contaminated or degraded. For example, electrodes may become contaminated as portions of the treated tissue adhere to the tissue-contacting surfaces of the electrodes. Also, a knife blade may become dull and less effective in transecting sealed tissue after repeated use, even in a single surgical procedure. In order to provide clean electrodes and a sharp knife for a particular surgical procedure, a brand new instrument is often used. Once the procedure is complete, the used instrument is discarded.

Instruments that are reusable for multiple procedures reduce the instrumentation costs per procedure. Providing a reusable electrosurgical forceps, however, presents various challenges. For example, the complexity of an electrosurgical forceps tends to result in fairly labor intensive cleaning procedures to prepare the forceps for subsequent use. Improper cleaning may result in dangerous contamination being introduced surgical site. Also, some reusable forceps have removable and replaceable components to provide clean surfaces for each use. Many of these instruments require arduous disassembly and reassembly procedures that require extensive training, and may discourage use of the instrument.

SUMMARY

The present disclosure describes a surgical instrument for treating tissue. The instrument includes an active electrode coupled to a source of electrosurgical energy and having a tissue-contacting surface on an exterior surface of the instrument such that the tissue-contacting surface of the active electrode may intimately engage tissue. A replacement electrode includes a tissue-contacting surface disposed in an interior cavity of the instrument, and a seal is defined between the active electrode and the interior cavity. Thus, the tissue-contacting-surface of the replacement electrode is isolated from contamination exposed to the exterior of the instrument. The active electrode is removable from the instrument to expose the tissue-contacting surface of the replacement electrode, and the replacement electrode is connectable to the source of electrosurgical energy when the active electrode is removed.

The active electrode may include a metal tape having a metallic substrate and an adhesive surface. The metallic substrate serves as the tissue-contacting surface and the adhesive surface serves to define the seal. The adhesive surface may include an electrically conductive adhesive that electrically couples the active electrode and the replacement electrode. Alternatively, an electrically insulative layer may be interspaced between the active electrode and the replacement electrode. The electrically insulative layer may include a plug disconnected from a remainder of the insulative layer, and the plug may be configured to adhere to the tissue-contacting surface of the replacement electrode upon removal of the remainder of the insulative layer. Thus, the plug may serve as a stop member to maintain a gap between the tissue-contacting surface of the replacement electrode and an opposing tissue-contacting surface.

The surgical instrument may include an elongated shaft extending proximally in relation to the active electrode, and the interior cavity may be formed within the elongated shaft. The active electrode may be disposed within a jaw member of a pair of opposing jaw members, and the pair of jaw opposing members may be movable between an open configuration wherein the jaw members are substantially spaced for receiving tissue and a closed configuration wherein the jaw members are closer together for clamping tissue therebetween.

According to another aspect of the disclosure, a surgical instrument includes an elongated shaft extending distally from a handle, and an end effector extending distally from the elongated shaft. The end effector includes an active contact surface and a replacement contact surface. The active contact surface is positioned to contact tissue in use, and a replacement contact surface is positioned relative to the active contact surface such that the presence of the active contact surface prohibits the replacement contact surface from contacting tissue in use. The active contact surface is removable from the end effector to permit the replacement contact surface to contact tissue in use.

The active contact surface may be configured as an active knife tip at a distal end of a reciprocating knife. The active knife tip may be distally movable through the end effector to cut tissue. The replacement contact surface may be configured as a replacement knife tip positioned proximally with respect to the active knife tip on the reciprocating knife. The surgical instrument may include an actuator disposed on the handle for advancing the reciprocating knife, and the actuator may mechanically engage an active drive surface on the reciprocating knife to distally move the active knife tip through the end effector. The actuator may be configured for disengagement from the active drive surface and engagement with a replacement drive surface disposed proximally of the active drive surface when the active knife tip is removed. Alternatively, the active contact surface may be configured as an electrode coupled to a source of electrosurgical energy.

The surgical instrument may include a protective sheath removably adhered to the elongated shaft. The protective sheath may be constructed of a flexible polymeric material.

According to yet another aspect of the disclosure, a surgical instrument includes an elongated shaft extending distally from a handle, and an end effector extending distally from the elongated shaft. The end effector includes a pair of opposing jaw members, and one or both of the jaw members is movable relative to the other to move the end effector between an open configuration wherein the jaws are substantially spaced for receiving tissue and a closed configuration wherein the jaw members are closer together for clamping tissue therebetween. A plurality of electrodes is restrained within an internal cavity defined in the elongated shaft, and an electrode receiving cavity is defined in at least one of the jaw members. The electrode receiving cavity is configured for releasably receiving an electrode and for establishing an electrical connection between the electrode and a source of electrosurgical energy. A dispensing mechanism is operable to establish a pathway between the internal cavity of the elongated shaft and the electrode receiving cavity to release an electrode into the electrode receiving cavity.

The electrodes may be configured as clips, and movement of the end effector to the closed configuration may induce plastic deformation of the clips. The clips may include an upper electrode and a lower electrode, and the upper and lower electrodes may be separated by an electrically insulative material. The electrode receiving cavity in the end effector may be configured for electrically coupling the upper electrode to a source of electrosurgical energy of a first potential and the lower electrode to a source of electrosurgical energy of a second potential. The dispensing mechanism may include a spring arranged to bias the plurality of electrodes in a distal direction toward the electrode receiving cavity.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

FIG. 2 is an enlarged, perspective view of the distal end of the instrument of FIG. 1 depicting a seal plate assembly having a plurality of removable, conductive electrodes arranged in adjacent layers;

FIG. 3A is a perspective view of an alternate embodiment of a seal plate assembly wherein insulation layers are interspaced between conductive electrode layers;

FIG. 3B is a perspective view of the seal plate arrangement of FIG. 3A depicting an uppermost insulation layer partially removed;

FIG. 6A is a partial, side view of an instrument having a plurality of seal plates dispensable from an elongated shaft;

FIG. 6B is a schematic view of jaw member having a distal opening for longitudinally ejecting seal plates;

FIG. 6C is a schematic view of an alternate embodiment of a jaw member having a pivot for rotationally ejecting seal plates;

FIG. 8B is a schematic view of an alternate embodiment of an instrument having an reciprocating knife with dispensable cutting tips;

FIG. 9 is a partial, side view of an instrument having a protective cover dispensable from an outer surface of an elongated shaft.

DETAILED DESCRIPTION

Figure 1:
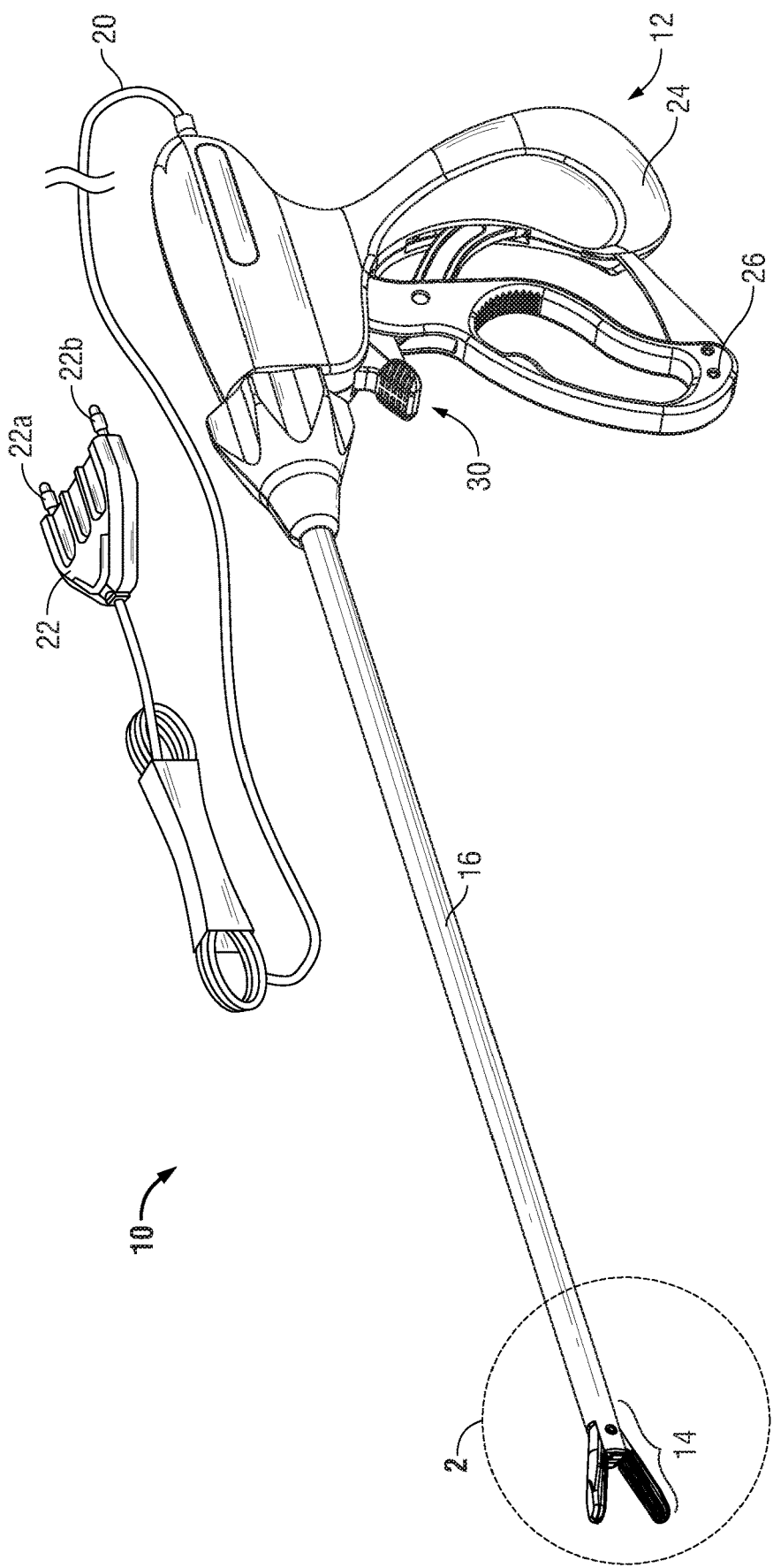
FIG. 1 is a perspective view of an endoscopic surgical instrument in accordance with the present disclosure having an end effector at a distal end.

Referring initially to FIG. 1, an embodiment of an electrosurgical instrument 10 is depicted. The instrument 10 includes a handle assembly 12 for remotely controlling an end effector 14 through an elongated shaft 16. Although this configuration is typically associated with instruments for use in laparoscopic or endoscopic surgical procedures, various aspects of the present disclosure may be practiced with traditional open instruments (see FIG. 10), and in connection with endoluminal procedures as well.

Handle assembly 12 is coupled to an electrosurgical cable 20, which may be used to connect the instrument 10 to a source of electrosurgical energy. The cable 20 extends to connector 22 including prong members 22a and 22b, which are configured to mechanically and electrically connect the instrument 10 to an electrosurgical generator (not shown). Each of the two prong members 22a and 22b may be associated with an opposite electrical potential (supplied by the generator) such that bipolar energy may be conducted through the cable 20, and through the instrument 10 to the end effector 14. In alternate embodiments (not shown), an instrument may include a battery and/or a generator disposed onboard the instrument. This arrangement obviates the need for electrosurgical cable 20, and permits operation of the instrument as a self-contained unit.

To control the end effector 14, the handle assembly 12 includes a stationary handle 24 and movable handle 26. The movable handle 26 may be separated and approximated relative to the stationary handle 24 to respectively open and close the end effector 14. A trigger 30 is also disposed on the handle assembly 12, and is operable to extend and retract a knife 52 (see FIG. 2) through the end effector 14. A footswitch (not shown) may be provided to initiate and terminate the delivery of electrosurgical energy to the end effector 14.

Referring now to FIG. 2, end effector 14 is depicted in an open configuration. Upper and lower jaw members 32 and 34 are separated from one another such that tissue may be received therebetween. The jaw members 32, 34 are pivotally coupled to the elongated shaft 16 by a pivot pin 36 extending therethrough. To engage the pivot pin 36, the upper and lower jaw members 32, 34 include respective proximal flanges 38, 40 extending into a bifurcated distal end of the elongated shaft 16. The proximal flanges 38, 40 are operatively associated with the movable handle 26 (FIG. 1) to open and close the jaw members 32, 34. Retraction of the movable handle 26 induces the jaw members 32, 34 rotate about the pivot pin 36 to move from the open configuration to a closed configuration where the jaw members 32, 34 are closer together (see FIG. 8A).

Various mechanisms may be provided to operatively associate the movable handle 26 with the proximal flanges 38, 40. For example, the movable handle 26 may be coupled to a reciprocating member (not shown) that extends through the elongated shaft 16 as described in commonly owned U.S. Pat. No. 7,255,697 to Dycus et al. The reciprocating member may engage cam slots (not shown) on each of the proximal flanges 38, 40 to change the position of both of the jaw members 32, 34 relative to the elongated shaft. This type of construction induces bilateral jaw motion. Unilateral constructions are also envisioned in which only one jaw member 32, 34 moves with respect to the elongated shaft.

The lower jaw member 34 includes a seal plate assembly 44 for delivering electrosurgical energy to tissue. Seal plate assembly 44 is electrically coupled to at least one of the prong members 22a, 22b of the connector 22 (FIG. 1) to receive electrosurgical energy of a first potential. The upper jaw member 32 may include an opposing seal plate assembly coupled to the other of the prong members 22a, 22b to receive electrosurgical energy of a second potential such that the end effector 14 is configured for delivering bipolar energy to tissue captured between the jaw members 32, 34. Alternatively, the end effector 14 may be configured for delivering monopolar energy to the tissue. In a monopolar configuration, the upper jaw member 32 may be electrically inactive or may deliver electrosurgical energy of the first potential.

The seal plate assembly 44 includes a first or active electrode 46 constructed as a metal tape. The active electrode 46 has a tissue-contacting surface 46a exposed on an exterior surface of the end effector 14 such that the active electrode 46 may contact tissue in use. An adhesive surface 46b on an opposite side of the electrode 46 adheres the active electrode 46 to a second or replacement electrode 48. The tissue-contacting surface 46a is constructed of a thin metallic substrate, such as silver, steel, gold or platinum. The thickness of the metal substrate may be from about 2 to about 3 mils such that a uniform electrical continuity is maintained across the entire tissue-contacting surface 46a. The adhesive surface 46b is also electrically conductive. The adhesive may be constructed of a mixture of a conventional copolymer adhesive and a sufficient ratio of metallic particles to provide a conductive and non-tacky adherence to the replacement electrode 48. The replacement electrode 48 of the seal plate assembly 44 may be constructed in a manner similar to the active electrode 46. The seal plate assembly 44 may be constructed of any number of similarly configured replacement electrodes 48 disposed adjacent one another in a layered arrangement.

In use, the active electrode 46 may be disposed so as to entirely overlay the replacement electrode 48. The adhesive layer 46b defines a seal, and thus maintains the replacement electrode 48 in an interior cavity isolated from the contamination on the exterior of the end effector 14. Electrosurgical energy may be conducted from the second electrode 48, through the adhesive and tissue-contacting surfaces 46b and 46a of the active electrode 46 to tissue clamped between the jaw members 32, 34. In any such electrosurgical procedure, there is a possibility of tissue adhesion and other forms of contamination that can render the active electrode 46 unsuitable for subsequent use. Once the procedure is complete, the user may sterilize the instrument 10 with the active electrode 46 in place, or alternatively, the user may simply peel the active electrode 46 from the seal plate assembly 44 to expose the replacement electrode 48. When an appropriate adhesive is selected for the adhesive surface 46b, no adhesive residue remains on the replacement electrode 48. In this manner, a new and clean electrode 46, 48 may be provided for each procedure without requiring a cumbersome assembly procedure, and while producing very little waste. In some instances, if excessive tissue adhesion occurs, for example, the user may wish interrupt a procedure to remove the active electrode 46, and continue the procedure using the clean second electrode 48.

The seal plate assembly 44 defines a knife channel 50 therein to permit longitudinal reciprocation of a knife blade 52. The knife channel 50 extends in a generally longitudinal direction along lower jaw member 34 to permit the knife blade 52 to traverse the knife channel 50, and to sever tissue clamped between the jaw members 32, 34. For example, once a tissue seal has been effected, a surgeon may advance the knife blade 52 distally through the knife channel 50 when the jaw members 32, 34 remain in the closed configuration clamping the tissue. In this manner, an accurate cut may be produced extends only through tissue that has been sealed. The transaction of tissue is discussed further below with reference to FIG. 8A.

Referring now to FIG. 3A, an alternate embodiment of a seal plate assembly 58 is depicted. The seal plate assembly 58 includes layers of electrically conductive electrodes 60a, 60b and 60c, and interspaced electrically insulative layers 62a, 62b and 62c. A lower surface of each of the layers 60a, 60b, 60c, 62a 62b, 62c is removably adhered to the immediately adjacent layer by an adhesive or other suitable means. Each of the insulative layers 62a, 62b, 62c includes discrete plugs 64 defined therein that are disconnected from the remainder of the insulative material. The plugs 64 are permanently adhered, or more securely affixed to, the immediate adjacent electrode layer 60a, 60b, 60c than the remainder of the insulative material. Thus, when an uppermost insulative layer 62a is removed from the seal plate assembly 58, as depicted in FIG. 3B, the plugs 64 remain affixed to the eclectically conductive electrode layer 60a.

The plugs 64 protrude a distance "G" from the electrode layer 60a and may serve as a stop member to maintain a particular separation distance between opposing tissue-contacting surfaces during the sealing process. For one embodiment, an gap distance "G" for generating an effective tissue seal may be between about 0.001 inches and about 0.006 inches. In a more particular embodiment, a gap distance "G" between about 0.002 inches and about 0.003 inches may be preferred. Providing interspaced insulative layers 62a, 62b, 62c of an appropriate thickness allows a new and clean stop member to be provided for each electrode layer 60a, 60b, 60c. After each instance of use, the exposed or active electrode layer, e.g., 60a, may be removed to prepare the seal plate assembly 58 for subsequent use. The number of remaining replacement electrodes 60b, 60c can provide an indication of the usage of the seal plate assembly 58.

Figure 4:
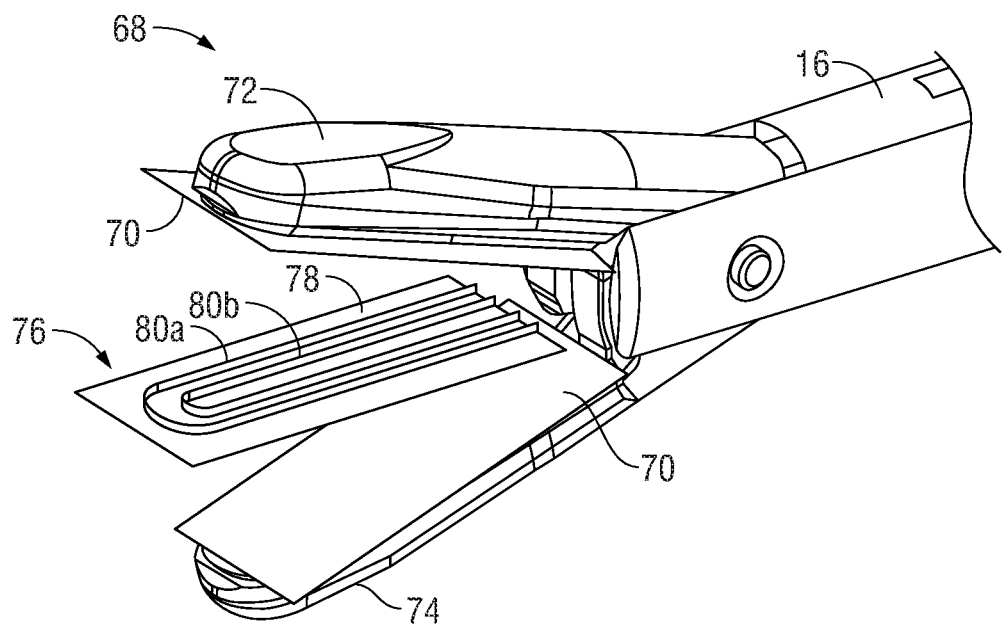
FIG. 4 is a perspective view of an alternate embodiment of an end effector depicting an installation of an additional conductive electrode layer with a cutting die.

Referring now to FIG. 4, an alternate embodiment of an end effector 68 is configured to receive a single new electrode pair prior to each instance of use. Oversized rectangular segments of a metallic tape 70 are positioned over opposed tissue facing surfaces of upper and lower jaw members 72, 74 such that the tape 70 makes electrical contact with the respective jaw member 72, 74. The metallic tape 70 may overhang the respective jaw members 72, 74, but should completely overlay intended electrode area. A cutting die 76 may then be introduced between the jaw members 72, 74. The cutting die 76 includes a flat support member 78 and cutting blades 80a and 80b protruding therefrom. The cutting blades 80a, 80b define the outside perimeter of the electrode and knife channel to be formed. One or both sides of the flat support member 78 may be equipped with cutting blades 80a, 80b to trim one or both segments of the metallic tape 70. The cutting die 76 may be positioned between the jaw members 72, 74, and then the end effector 68 may be moved to a closed configuration such that the jaw members 72, 74 are clamped onto the cutting die 76. The clamping force from the jaw members 72, 74 is employed to sever the metallic tape 70 against the blades 80a, 80b to produce precisely shaped electrodes from the metallic tape 70.

After the end effector 68 is used in an electrosurgical procedure, the metallic tape 70 may be removed, and the process may be repeated to prepare the end effector 68 for subsequent use. Since no alignment of the metallic tape 70 is required, the process is a repeatable method of refurbishing the end effector 68 that may be accomplished with minimal training. This procedure may also be employed to affix additional layers of electrodes to the seal plate assembly 44 as described above with reference to FIG. 2.

Figure 5:
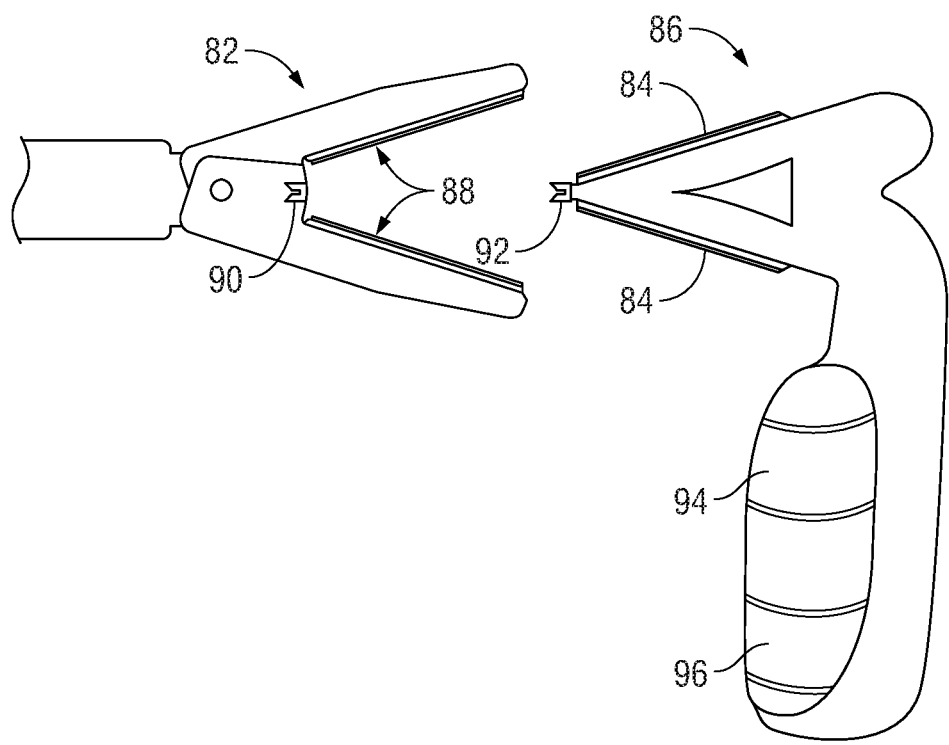
FIG. 5 is a side view of an alternate embodiment of an end effector depicting an installation of a seal plate assembly with a hand tool.

Referring now to FIG. 5, in an alternate embodiment, an end effector 82 is configured to receive a new set of electrodes 84 from a hand tool 86. The end effector 82 is provided with a pair of electrode receiving cavities or slots 88 to receive, restrain and to make the necessary electrical connections with the electrodes 84. To facilitate alignment of the electrodes 84 with the electrode receiving slots 88, an alignment slot 90 is disposed on the end effector 82 to engage an alignment key 90 on the hand tool 86. When the alignment key 92 engages the key slot 90, the proper positioning of the hand tool 86 with respect to the end effector 82 is achieved. The electrodes 84 are securely restrained in the hand tool 86 in an orientation corresponding to an open configuration of the end effector 82 to facilitate exchanging the electrodes 84 with the end effector 82. The hand tool 86 includes a first actuator, such as button 94, which is operable to release the electrodes 84 from the hand tool 86 into the electrode receiving slots 88. Operation of the button 94 may be disabled when the alignment key 92 is not properly engaged with the alignment slot 90. The end effector 82 may be moved toward a closed position using instrument actuators such as the movable handle 26 (FIG. 1) to lock the electrodes 84 in place. New electrodes 84 may thus be installed in the end effector 82 without being handled directly.

The hand tool 86 may also be used to remove used electrodes 84 from the end effector 82. A second actuator, such as button 96 is operable to grasp the electrodes 84 when the alignment key 92 is properly engaged with the alignment slot 90.

Referring now to FIG. 6A, an instrument 100 includes exposed or active seal plates 102a, and a plurality of replacement seal plates 102b restrained in and dispensable from an interior cavity defined in elongated shaft 104. The seal plates 102a, 102b may be configured as single electrodes formed from a single sheet of an electrically conductive metal, or alternatively, the seal plates 102a, 102b may be constructed in a layered configuration as described above with reference to FIGS. 2 and 3A.

The elongated shaft 104 provides a sealed and protective interior storage environment to maintain the replacement seal plates 102b in a clean condition until needed. The replacement seal plates 102b are arranged in two separate longitudinal rows corresponding to upper and lower jaw members 106, 108. Under the influence of a spring 110, which biases the replacement seal plates 102b in a distal direction, the replacement seal plates 102b abut one another within the elongated shaft 104. A pair of distal-most replacement seal plates 102b abuts a dispensing mechanism 112. The dispensing mechanism 112 includes a pair of gates 114, each having a passageway 114a defined therethrough. The gates 114 are biased in a laterally outward direction by a spring 116.

Prior to each instance of use, a new and clean pair of replacement seal plates 102b may be dispensed into the jaw members 106, 108. First, the active seal plates 102a may be removed by any means including the hand tool 86 discussed above with reference to FIG. 5. Then, the dispensing mechanism 112 may be actuated by pressing the gates 114 laterally inward to compress the spring 116. The passageways 114a are thereby moved into alignment with the rows of seal plates 102, and a pathway is established between the interior cavity of elongated shaft 104 and the jaw members 106, 108. A pair of seal plates 102 is permitted to pass through the passageways 114a under the influence of the spring 110. Each seal plate 120 moves into a respective cavity 120, 122 extending between the elongated shaft 104 and a respective electrode receiving slot 124, 126. A first seal plate 120 moves into electrode receiving slot 124 defined in upper jaw 106, and makes electrical contact with a source of electrosurgical energy of the first potential (+). A second seal plate 120 moves into electrode receiving slot 126 defined in lower jaw member 108, and makes electrical contact with a source of electrosurgical energy of the second potential (−). In this manner a bipolar instrument may be provided.

Referring now to FIG. 6B, an alternate embodiment of a jaw member 106a is configured for dispensing the active seal plate 102a and the replacement seal plate 102b in a longitudinal direction as indicated by arrow 106b. The jaw member 106a includes a distal opening 106c that is in general alignment with a compression spring 110a. Since a distal end of the replacement seal plate 102b abuts a proximal end of the active seal plate 102a, a biasing force provided by the compression spring 110a may be transmitted through the replacement seal plate 102b to the active seal plate 102a. Thus, the biasing force of the compression spring 110a may be employed to eject the active seal plate 102a straight through the distal opening 106c at the end of the jaw member 106a while simultaneously advancing the replacement seal plate 102b.

Electrosurgical energy may also be transmitted through the replacement seal plate 102b to the active seal plate 102a. Electrosurgical energy, e.g., energy of the first potential (+), may be delivered to the replacement seal plate 102b from a source of electrosurgical energy (not shown). The source of electrosurgical energy may be positioned at a convenient location, e.g., at a location proximal with respect to the active seal plate 102a. Since the distal end of the replacement seal plate 102b abuts the proximal end of the active seal plate 102a, the replacement seal plate 102b provides an electrically conductive pathway for the electrosurgical energy to be transmitted to the active seal plate 102a.

Referring now to FIG. 6C, an alternate embodiment of a jaw member 108a is configured for dispensing an active seal plate 102c and replacement seal plates 102d in a rotational direction as indicated by arrow 108b. The jaw member 108a includes a distal abutment 108c that provides a pivot about which the seal plates 102c, 102d may rotate. Each of the seal plates 102c 102d includes an angled ramp 102e at the distal end thereof. The angled ramp 102e of the active seal plate 102c provides clearance to facilitate rotational motion of the seal plate 102c about the abutment 108c. The angled ramps 102e on the replacement seal plates 102d engage the proximal end of the active seal plate 102c, and under the influence of compression spring 110a, drive the proximal end of the active seal plate 102c from the jaw member 108a. Since the distal-most replacement seal plate 102d abuts the proximal end of the active seal plate 102c, the replacement seal plates 102b provide an electrically conductive pathway for the delivery of electrosurgical energy to the active seal plate 102c as described above with reference to FIG. 6B.

Figure 7:
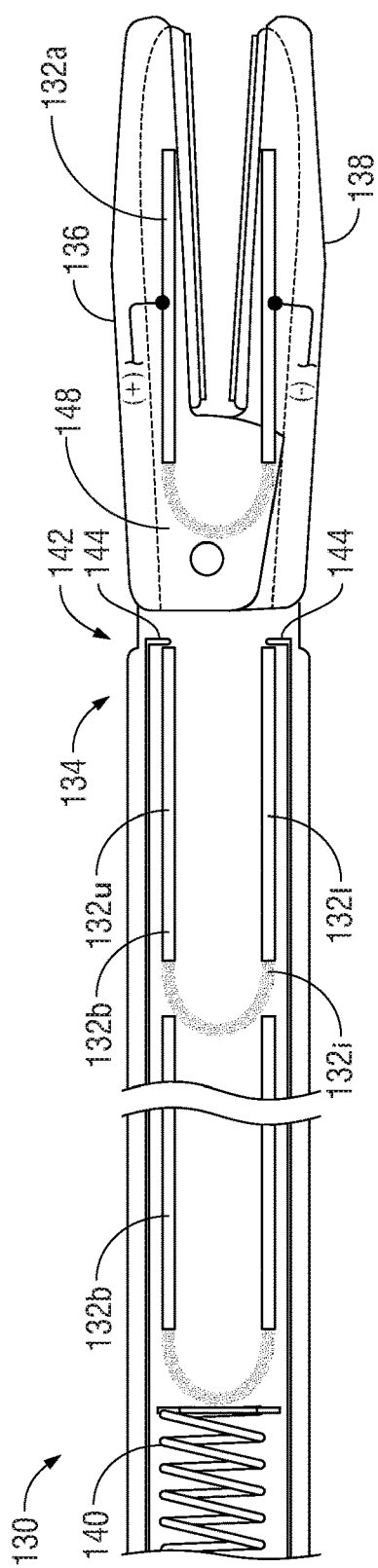
FIG. 7 is a partial, side view of an alternate embodiment of an instrument having a plurality of seal plates dispensable from an elongated shaft, wherein the seal plates are configured as clips.

Referring now to FIG. 7, an alternate embodiment of an instrument 130 includes an active seal plate assembly 132a and a plurality of replacement seal plate assemblies 132b dispensable from elongated shaft 134. The seal plate assemblies 132a, 132b are configured as clips or staples that may be used to electrosurgically treat tissue, and thereafter remain in the tissue to provide a mechanical clamping force thereto. Each seal plate assembly 132 includes an upper electrode 132u connectable to a source of electrosurgical energy of the first potential (+) by making contact with an upper jaw member 136, and a lower electrode 132l connectable to a source of electrosurgical energy of the second potential (−) by making contact with a lower jaw member 138. The upper and lower electrodes 132u, 132l are coupled to one another with a flexible, eclectically insulative material 132i. The seal plate assemblies 132a, 132b may be constructed of a bioabsorbable material, and may contain a medicament to promote tissue healing.

The replacement seal plate assemblies 132b abut one another under the influence of a spring 140, which biases the seal plate assemblies 132b in a distal direction. A distal end of a distal-most seal plate assembly 132b in the elongated shaft 134 abuts a dispensing mechanism 142. The dispensing mechanism 142 includes a pair of hooks 144 each extending toward a proximal end of the instrument 130. The hooks 144 may be actuated from a proximal end of the instrument 130 to shift in a laterally outward direction to permit passage a replacement seal plate assembly 132b into an electrode receiving cavity 148 defined in the jaw members 136, 138.

In use, the active seal plate assembly 132a may be clamped onto tissue by the jaw members 136, 138 during an initial use of the instrument 130. Thereafter a replacement seal plate assembly 132b may be dispensed from elongated shaft 134 into the electrode receiving cavity 148 where the electrodes 132u and 132l of the replacement seal plate assembly 132b makes electrical contact with the jaw members 136, 138. The jaw members 136, 138 may be moved to a closed configuration to plastically deform the seal plate assembly 132 about tissue, and electrosurgical energy may be delivered to the tissue through the replacement seal plate assembly 132b. The jaw members 136, 138 may be moved to an open configuration to eject the seal plate assembly 132b from the cavity 148. Since the seal plate assembly 132b is plastically deformed, the seal plate assembly 132b remains clamped about the tissue. This process may be repeated for each seal plate assembly 132b restrained in the elongated shaft 134.

Figure 8A:
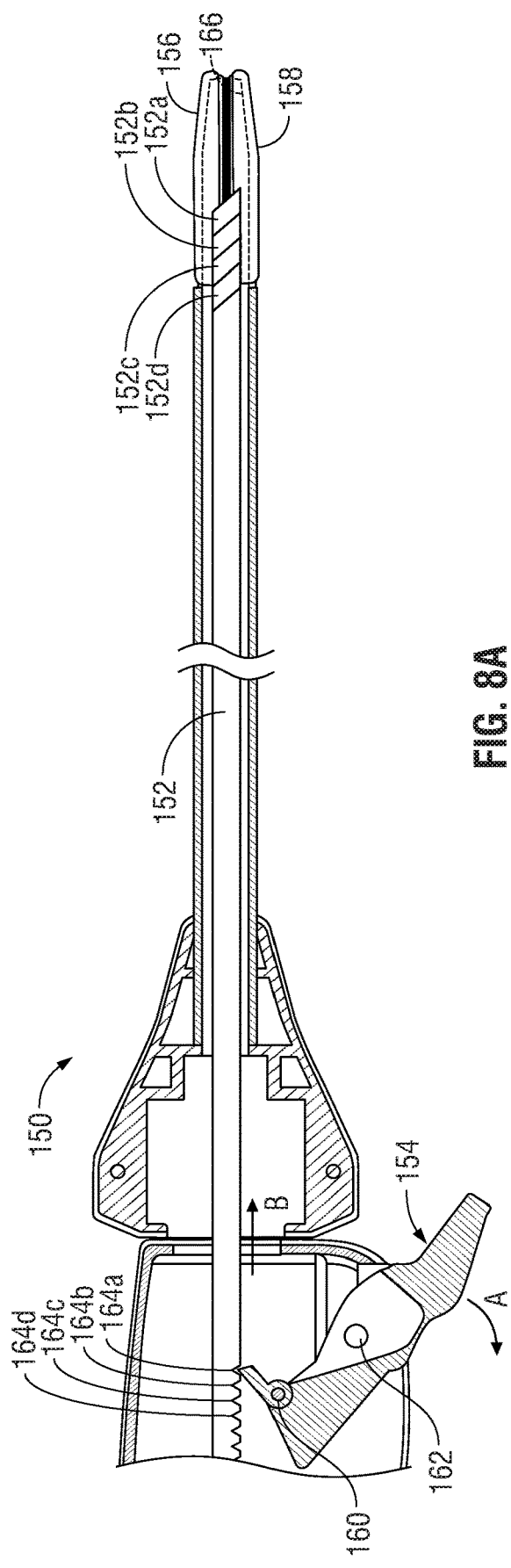
FIG. 8A is a partial, side view of an instrument having a reciprocating knife with dispensable cutting tips.

Referring now to FIG. 8A, an alternate embodiment of an instrument 150 includes a reciprocating knife 152 having dispensable tips 152a, 152b, 152c, and 152d. An active knife tip 152a defines a distal-most cutting surface of the reciprocating knife 152, and replacement tips 152b, 152c, and 152d are disposed proximally with respect to the active knife tip 152a. The reciprocating knife 152 extends between a trigger 154 at a proximal end of the instrument 150 and jaw members 156, 158. The trigger 154 is coupled to a pawl 160 that engages the knife 152 about a first or active drive notch or drive surface 164a. The trigger 154 may be retracted in the proximal direction of arrow "A" to pivot about a pin 162 and drive the pawl 160 in the distal direction of arrow "B." The pawl 160 bears against active drive notch 164a of the knife 152, and thus, the active knife tip 152a may be induced to traverse a knife channel 166 in the distal direction of arrow "B" to sever tissue captured between the jaw members 156, 158. When this process is repeated several times throughout an electrosurgical procedure, the active knife tip 152a may become contaminated or dull.

Since the active knife tip 152a is disposed distally of the replacement knife tips 152b, 152c, and 152d, the presence of the active knife tip 152a prohibits a forward cutting edge of the replacement knife tips 152b, 152c, 152d from contacting tissue and becoming dull. When the electrosurgical procedure is complete, the active knife tip 152a may be severed from the knife 152 to reveal a clean and sharp replacement knife tip 152b. The knife 152 may be configured such that a score line or an area of relative weakness exists between the tips 152a, 152b, 152c, and 152d and each of the tips 152a, 152b, 152c, and 152d may be chipped off from the remainder of the knife 152 at a precise location.

The removal of each of the knife tips 152a, e.g., reduces the overall length of the knife 152. To ensure the new knife tip 152b, e.g., traverses the entire knife channel 166, an adjustment is made at the proximal end of knife 152. The pawl 160 may be disengaged from the active drive notch 164a and may be moved to engage a supplementary or replacement drive notch 164b. Additional drive notches 164c, 164d are provided to accommodate knife tips 152c, and 152d.

Referring now to FIG. 8B, an alternate embodiment of an instrument 150a includes an alternate mechanism for compensating for a change in length of a knife 152e. The knife 152e includes dispensable knife tips 152f, 152g, 152h and 152i that may be severed from the knife 152e to reveal a clean and sharp replacement knife tip, e.g., tips 152g, 152h and 152i. As described above with reference to FIG. 8A, the removal of the knife tips 152f, 152g, 152h and 152i reduce the overall length of the knife 152e, and thus an adjustment may be necessary to ensure that the replacement knife tips e.g., tips 152g, 152h and 152i, traverse the entire knife channel 166a in subsequent uses.

The knife 152e is operatively coupled to a trigger 154a by a connecting rod 160a. The connecting rod 160a is pivotally coupled to the knife 152e by a pivot pin 160b, and pivotally coupled to the trigger 154a by a connecting pin 160c. The trigger 154a is pivotally supported on a stationary support 162a, which provides a stationary reference with respect to the instrument 154a. The stationary support 162a also supports a compression spring 162b that maintains the connecting pin 160c of the connecting rod 160a in one of a series of drive slots 164e, 164f, 164g, 164h defined on an upper portion of the trigger 154a. The drive slots 164e, 164f, 164g and 164h are each positioned on the trigger 145a to correspond with a respective knife tip 152f, 152g, 152h and 152i such that the respective knife tip 152f, 152g, 152h, 152i may traverse the entire knife channel 166a.

In use, the trigger 154a may be retracted in the proximal direction of arrow "C" to pivot about the stationary support 162a. The upper portion of the trigger 154a swings the direction of arrow "D," which drives the connecting rod 160a and the knife 152e in the distal direction of arrow "E" through the knife channel 166a. At the end of the knife stroke, e.g., when the knife 152e reaches the distal end of the knife channel 166a, the upper portion of the trigger 154a reaches a distal-most position. In this distal-most position, the connecting pin 160c is permitted to slip from one drive slot, e.g., slot 164e, to another drive slot, e.g., 164f under the influence of the compression 162b. Thus, when a knife tip, e.g., 152f, is removed from the knife 152e the drive slot 164f corresponding to the next available knife tip 152g will drive the connecting rod 160a and knife 152e distally through the knife channel 166a upon subsequent actuation of the trigger 154a. In this manner, the instrument 150a automatically compensates the change in the length of the knife 152e due to the removal of knife tips 152f, 152g, 152h and 152i.

Referring now to FIG. 9, an alternate embodiment of an instrument 170 includes a protective sheath 172 provided over elongated shaft 174. The protective sheath 172 releasably affixed to the elongated shaft 174 to provide protection against contamination during use of the instrument 170. After use in an electrosurgical procedure, the instrument 170 may be prepared for subsequent use by removing the sheath 172, and thereby removing any contamination adhered to the sheath 172. A tab 176 protrudes from a longitudinal edge of the sheath 172, and is provided to facilitate removal of the sheath 172 along a seam 178.

The sheath 172 overlies a supplementary or replacement sheath 180. The sheaths 172, 180 may be adhered to one another with a removable adhesive, by electrostatic bonding or other suitable means that permits sheath 172 to be removed as described above. The supplementary sheath 180 remains uncontaminated during the initial use, and provides protection to the elongated shaft 174 during subsequent usage. Any number of additional sheaths (not shown) may be provided in a layered configuration for any number of subsequent uses.

The sheaths 172, 180 may be constructed of a flexible polymeric material, and may permit usage of an actuator such as button 182 therethrough. The button 182 may be operable, for example, to dispense seal plates as described above with reference to FIG. 6A. A protective sheath may be provided over other parts of the instrument 170 in addition to the elongated shaft 174. For example, a handle assembly (see FIG. 1) may be equipped with removable sheaths to provide protection thereto.

Figure 10:
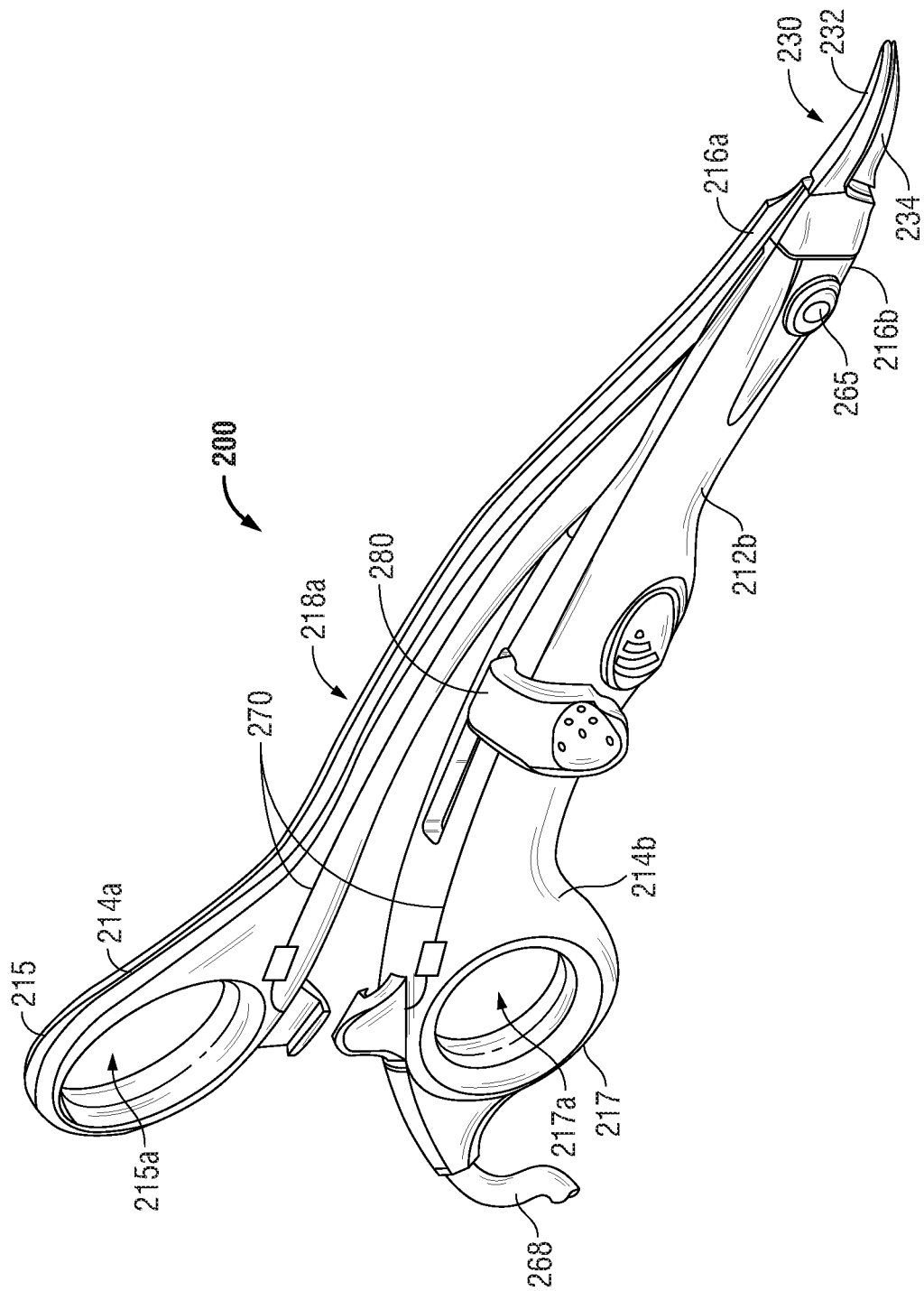
FIG. 10 is an open instrument in accordance with the present disclosure.

With regard to FIG. 10, a forceps 200 configured for use in various open surgical procedures may also incorporate many of the features described above. Forceps 200 includes a pair of opposing elongated shafts 212a and 212b having an end effector assembly 230 attached to the distal ends 216a and 216b thereof, respectively. End effector assembly 230 is similar in design to end effector assembly 14 described above with reference to FIG. 1. End effector assembly 230 and includes pair of opposing jaw members 232 and 234 that are pivotably connected about a pivot pin 265 and which are movable relative to one another to grasp tissue. The jaw members 232 and 234 may be configured to receive seal plate assemblies 44, 58 as described above with reference to FIGS. 2, 3A and 3B. The elongated shafts 212a and 212b may be configured to house and dispense seal plates 102, 132 as described above with reference to FIGS. 6 and 7, for example.

Each shaft 212a and 212b includes a handle 215 and 217, respectively, disposed at the proximal end 214a and 214b thereof which each define a finger hole 215a and 217a, respectively, therethrough for receiving a finger of the clinician. Finger holes 215a and 217a facilitate movement of the shafts 212a and 212b relative to one another which, in turn, pivot the jaw members 232 and 234 from an open position wherein the jaw members 232 and 234 are disposed in spaced relation relative to one another to a clamping or closed position wherein the jaw members 232 and 234 cooperate to grasp tissue therebetween.

An electrosurgical cable 268 couples the instrument 200 to a source of electrosurgical energy, and conductive pathways 270 are provided to transmit electrosurgical energy to the jaw members 232, 234. A knife trigger 280 is provided to induce a knife (not shown) to transect tissue captured between the jaw members 232, 234. A knife similar to knife 152 described above with reference to FIG. 8A may be provided.

Although the foregoing disclosure has been described in some detail by way of illustration and example, for purposes of clarity or understanding, it will be obvious that certain changes and modifications may be practiced within the scope of the appended claims.

What is claimed is:

1. A surgical instrument comprising:
an elongated shaft defining an internal cavity;
a plurality of electrodes restrained within the internal cavity of the elongated shaft;
an end effector extending distally from the elongated shaft;
an electrode receiving cavity defined in the end effector, the electrode receiving cavity configured for releasably receiving at least one electrode of the plurality of electrodes from the internal cavity of the elongated shaft and for establishing an electrical connection between the at least one electrode of the plurality of electrodes and a source of electrosurgical energy; and
a dispensing mechanism configured to selectively permit and restrict passage of one electrode of the plurality of electrodes from the internal cavity of the elongated shaft into the electrode receiving cavity, wherein the dispensing mechanism includes at least one hook configured to selectively engage a distal portion of the one electrode, the at least one hook being movable between a laterally inward position where the hook restricts passage of the one electrode from the internal cavity of the elongated shaft into the electrode receiving cavity, and a laterally outward position where the hook permits passage of the one electrode from the internal cavity of the elongated shaft into the electrode receiving cavity.

2. The surgical instrument according to claim 1, wherein each of the plurality of electrodes is configured as a clip.

3. The surgical instrument according to claim 2, wherein each clip includes an upper electrode, a lower electrode, and an electrically insulative material disposed between the upper electrode and the lower electrode.

4. The surgical instrument according to claim 1, wherein the end effector includes a pair of opposing jaw members, at least one of the jaw members is movable relative to the other to move the end effector between an open configuration wherein the opposing jaw members are substantially spaced for receiving tissue and a closed configuration wherein the opposing jaw members are closer together for clamping the tissue therebetween.

5. The surgical instrument according to claim 4, wherein each of the plurality of electrodes is configured as a clip, and wherein movement of the end effector to the closed configuration induces plastic deformation of at least one clip.

* * * * *